(12) United States Patent
Christiansen et al.

(10) Patent No.: US 8,226,696 B1
(45) Date of Patent: Jul. 24, 2012

(54) LIGHT PULSE GENERATING APPARATUS AND COSMETIC AND THERAPEUTIC PHOTOTREATMENT

(75) Inventors: Kare Christiansen, Gentofte (DK); Hugin Hansen, Hørsholm (DK)

(73) Assignee: Ellipse A/S, Horsholm (DK)

( * ) Notice: Subject to any disclaimer, the term of this patent is extended or adjusted under 35 U.S.C. 154(b) by 1212 days.

(21) Appl. No.: 09/097,383

(22) Filed: Jun. 16, 1998

(30) Foreign Application Priority Data

Jun. 16, 1997 (DK) .................................. 1997 00703
Nov. 24, 1997 (GB) .................................. 9724775.3

(51) Int. Cl.
*A61N 5/06* (2006.01)
(52) U.S. Cl. .......................................... 607/88; 607/90
(58) Field of Classification Search ............ 606/2, 3–19; 607/88–96
See application file for complete search history.

(56) References Cited

U.S. PATENT DOCUMENTS

| | | | |
|---|---|---|---|
| 1,651,385 A | | 12/1927 | Goodrich |
| 1,677,016 A | * | 7/1928 | Berry ............................... 607/93 |
| 3,327,712 A | | 6/1967 | Kaufman et al. |
| 3,693,623 A | | 9/1972 | Harte et al. |
| 3,703,176 A | * | 11/1972 | Vassiliadis et al. ............... 606/3 |
| 4,224,944 A | | 9/1980 | Roberts |
| 4,388,924 A | | 6/1983 | Weissman et al. |
| 4,603,422 A | * | 7/1986 | Fletcher .......................... 372/53 |
| 4,608,978 A | | 9/1986 | Rohr |
| 4,671,285 A | | 6/1987 | Walker |
| 4,784,135 A | | 11/1988 | Blum et al. |
| 4,829,262 A | | 5/1989 | Furumoto |
| 4,860,172 A | | 8/1989 | Schlager et al. |
| 4,876,694 A | * | 10/1989 | Hughes ........................... 372/93 |
| 4,930,504 A | | 6/1990 | Diamantopoulos et al. |
| 4,930,505 A | | 6/1990 | Hatje |
| 4,940,466 A | | 7/1990 | Paduano et al. |
| 4,966,144 A | | 10/1990 | Rochkind et al. |
| 5,059,192 A | | 10/1991 | Zaias |

(Continued)

FOREIGN PATENT DOCUMENTS

CH                416861                7/1966

(Continued)

OTHER PUBLICATIONS

"Photodynamic Therapy of Tumors with Heradecafluoro Zinc Phthalocyanine formulated in PEC-Coated Poly(Lactotal) Nanoparticles" by Allemann et al.; Int J. Cancer vol. 66 pp. 821-824 (1996).*

(Continued)

*Primary Examiner* — David Shay
(74) *Attorney, Agent, or Firm* — Pillsbury Winthrop Shaw Pittman LLP

(57) ABSTRACT

Apparatus for therapeutic or cosmetic photo-treatment comprises a flash lamp and a lamp operating circuit. The lamp is cooled by water in contact with the lamp which acts as an infra-red filter to reduce skin burning. Light from the lamp reaches the skin through a light guide which has a convex curved end to focus the light and to press away haemoglobin in the target area or has a concave end to reduce pressure on the skin depending on the desired treatment. Relatively long and low power square shaped power pulses drive the lamp to produce light output pulses adapted to the relaxation time of the target structure to maximize the heating of the target while minimizing heating of the skin surface. Target structures may be blood vessels or hair follicles. Automatic detection of a glass filter may be provided.

14 Claims, 6 Drawing Sheets

U.S. PATENT DOCUMENTS

| | | | |
|---|---|---|---|
| 5,066,293 A | 11/1991 | Furumoto | |
| 5,191,261 A | 3/1993 | Mass | |
| 5,217,455 A | 6/1993 | Tan | |
| 5,259,380 A | 11/1993 | Mendes et al. | |
| 5,290,273 A | 3/1994 | Tan | |
| 5,304,170 A | 4/1994 | Green | |
| 5,312,395 A | 5/1994 | Tan et al. | |
| 5,320,618 A | 6/1994 | Gustafsson | |
| 5,344,433 A | 9/1994 | Talmore | |
| 5,358,503 A | 10/1994 | Bertwell et al. | |
| 5,405,368 A | 4/1995 | Eckhouse | |
| 5,453,883 A | 9/1995 | Chazallet | |
| 5,522,814 A | 6/1996 | Bernaz | |
| 5,620,478 A * | 4/1997 | Eckhouse | 606/9 |
| 5,626,631 A | 5/1997 | Eckhouse | |
| 5,630,811 A | 5/1997 | Miller | |
| 5,643,334 A | 7/1997 | Eckhouse et al. | |
| 5,647,886 A | 7/1997 | Kitazawa et al. | |
| 5,655,547 A | 8/1997 | Karni | |
| 5,683,380 A | 11/1997 | Eckhouse et al. | |
| 5,707,401 A | 1/1998 | Talmore | |
| 5,720,772 A | 2/1998 | Eckhouse | |
| 5,735,844 A * | 4/1998 | Anderson et al. | 606/9 |

FOREIGN PATENT DOCUMENTS

| | | |
|---|---|---|
| DE | 692 907 | 6/1940 |
| DE | 911 525 | 5/1954 |
| DE | 2717421 | 11/1978 |
| DE | 3116958 | 12/1982 |
| DE | 3134953 | 3/1983 |
| DE | 3220962 | 12/1983 |
| DE | 38 03 763 | 8/1989 |
| EP | 052765 | 6/1982 |
| EP | 0 485 864 | 5/1992 |
| EP | 0 565 331 | 10/1993 |
| EP | 726083 | 8/1996 |
| EP | 763371 | 3/1997 |
| EP | 765673 | 4/1997 |
| EP | 765674 | 4/1997 |
| EP | 783904 | 7/1997 |
| EP | 788765 | 8/1997 |
| EP | 788814 | 8/1997 |
| EP | 822629 | 2/1998 |
| EP | 826335 | 3/1998 |
| EP | 827716 | 3/1998 |
| FR | 2590791 | 6/1987 |
| GB | 1513057 | 6/1978 |
| GB | 2049907 | 12/1980 |
| GB | 2208803 | 4/1989 |
| GB | 2212010 | 7/1989 |
| GB | 2308307 | 6/1997 |
| RU | 2001643 | 10/1993 |
| RU | 2072879 | 2/1997 |
| SU | 1724269 | 4/1992 |
| WO | 84/04463 | 11/1984 |
| WO | 89/00027 | 1/1989 |
| WO | 95/15725 | 6/1995 |
| WO | 96/41579 | 12/1996 |
| WO | 97/00098 | 1/1997 |

OTHER PUBLICATIONS

"High Performance Flash and Arc Lamps" Perkin Elner Optoelectronic.*

Data sheet for Schoot OG550 filter from www.us.schott.com; Jun. 1997.*

Patent Abstracts of Japan, 9-10328, Jan. 1997, Tsuji, et al.

Arons, "Laser Hair Removal Seen as Next Boom Market", Medical Laser Report, Apr. 1997, pp. 4-6.

Lahaye, et al., "Optimal Laser Parameters for Port Wine Stain Therapy: A Theoretical Approach", Phys. Med. Biol., 1985, vol. 30, No. 6., pp. 573-587.

Van Gemert, et al., "Treatment of Port-Wine Stains: Analysis", Medical Instrumentation, Aug. 1987, vol. 21, No. 4, pp. 213-217.

Grossman, et al., "Damage to Hair Follicles by Normal-Mode Ruby Laser Pulses", Journal American Academy of Dermatology, Dec. 1986, pp. 889-894.

R. Rox Anderson, MD, "Hair Removal Using Light", Palomar Medical, Mar. 1997, unnumbered, 2 pages.

R. Rox Anderson, MD, "Safety and Efficacy of the Polomar Ruby Laser for Hair Removal", Palomar Medical, Mar. 1997, unnumbered, 2 pages.

ESC Medical System, "PhotoDerm VL", probably 1996, 6 pages, unnumbered.

L. Milgrom et al., "Light Ahead", Chemistry in Britain, May 1998, pp. 45-50.

EG&G Electro-Optics, 15, author unknown, Jan. 1995, 1 page.

P. Bjerring et al., "Skin Reflectance Spectrophotometry" Photodermatology; 1987 pp. 167-171.

* cited by examiner

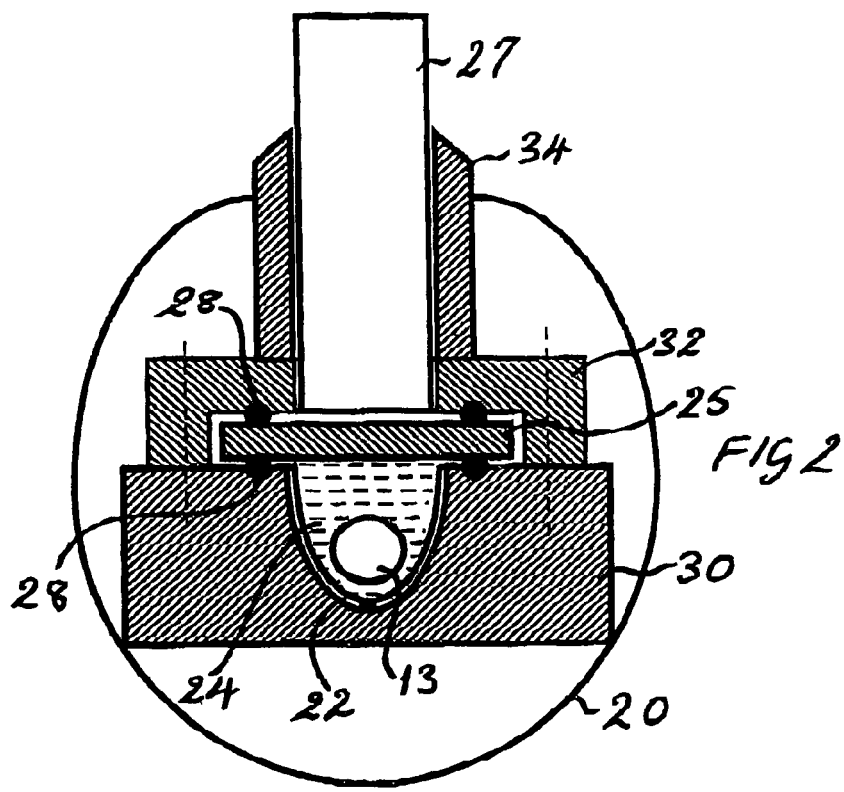
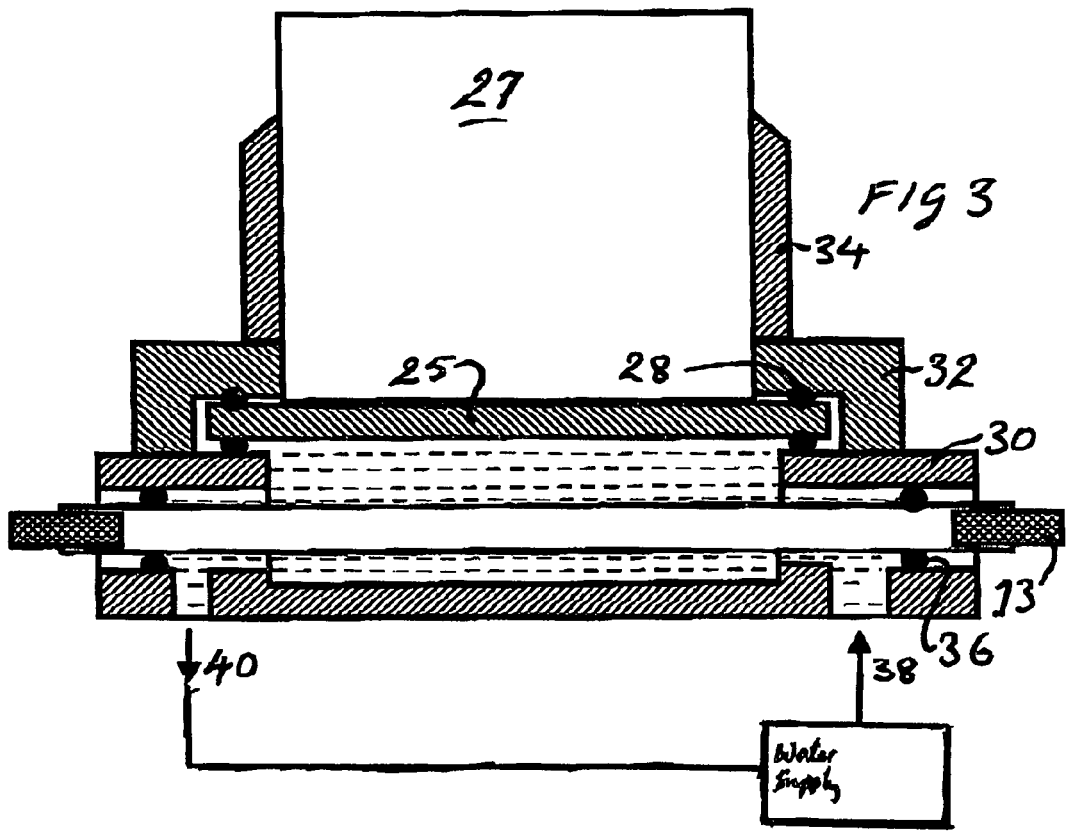

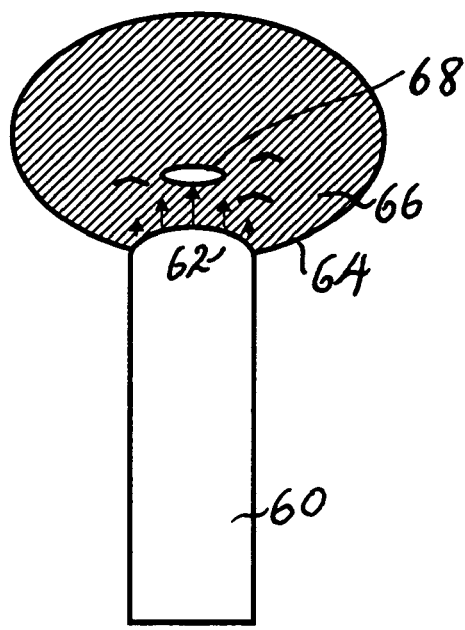
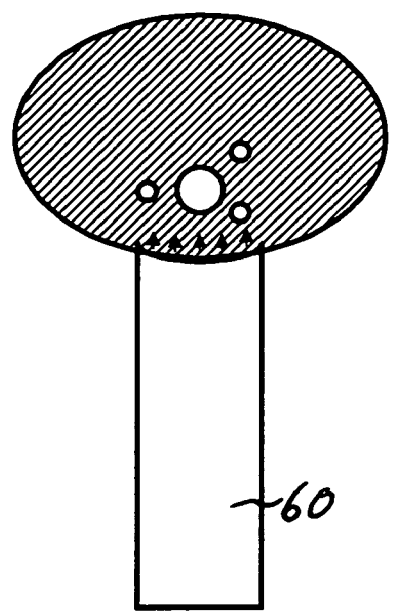
FIG 10  FIG 11
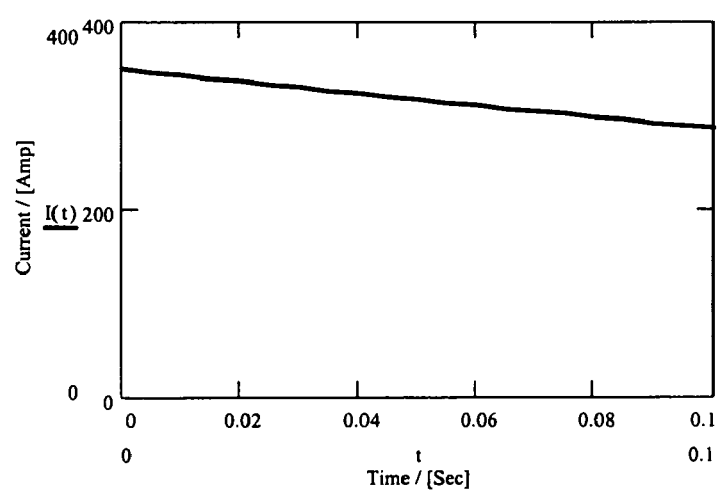
FIG 4

Thin Hair:
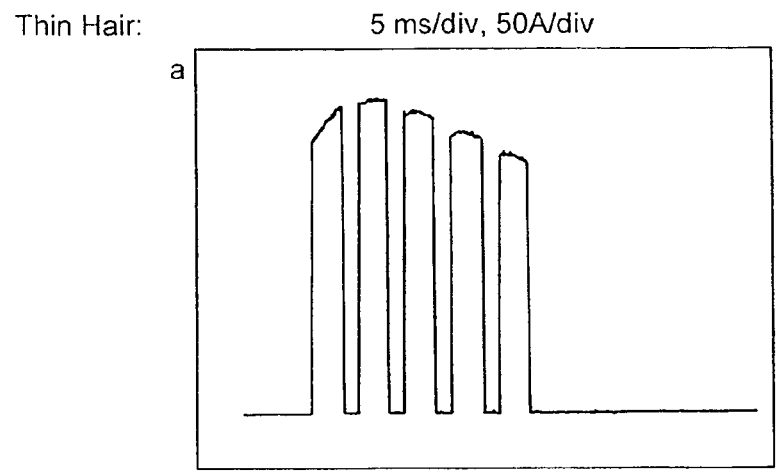
Pulse time=3ms, Pulse delay=1.5ms, N=5
Normal Hair:
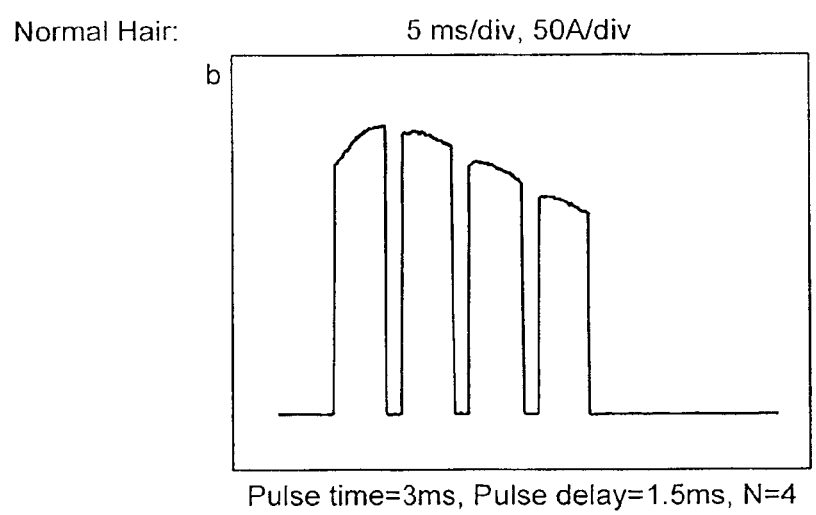
Pulse time=3ms, Pulse delay=1.5ms, N=4
Thick Hair:
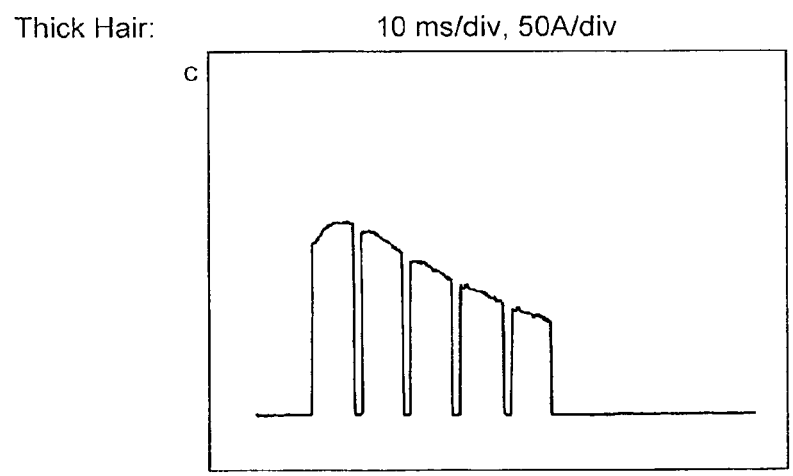
FIG. 6

LIGHT PULSE GENERATING APPARATUS AND COSMETIC AND THERAPEUTIC PHOTOTREATMENT

CROSS REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

The present invention relates to apparatus for producing light pulses and to apparatus and methods using light for cosmetic or therapeutic photo-treatment.

Apparatus of this type may be used for therapeutic purposes including treatment for psoriasis, vascular traumas, telangiectasis, capillary hemangioma, cancerous cells, port-wine stains, and birthmarks and also for depilation.

WO 091/15264 describes a device for treatment of undesired skin disfigurements, which apparatus comprises a gas filled lamp and an optical filter. The lamp is powered by a capacitor charged to about 2,000 volts, which is sufficient for generating a pulse with a pulse duration between ½ and 1 ms.

EP 0 565 331 A2 describes a therapeutic treatment device which includes a gas filled flash lamp and a set of optical filters. The power circuit includes three different pulse forming networks, which may be triggered selectively or successively. Each pulse forming network includes a capacitance and an inductance and a relay contact to trigger the discharge. The three networks are designed for providing different pulse widths. The capacitors are charged to a voltage, typically in the range of from 500 volts to 5 kilovolts.

EP 0 736 308 A2 discloses a method and an apparatus for depilation, wherein an apparatus of a similar kind is used. According to this publication an energy fluence in the order of from 10 to 100 J/cm$^2$ is used for the purpose of killing hair follicles without burning the surrounding skin. The publication also suggests the use of an optically transparent water-based gel applied to the skin prior to treatment and serving the purpose of providing a heat sink to prevent hyperthermia in the skin.

We have found several limitations and problems in devices and methods according to the prior art. Damage to the skin or burns occur very easily, making it difficult to find an energy level at which the pulses will be effective but will not harm the skin. Further the amount of heat absorbed in the optical filters may be excessive, frequently leading to destruction of the filters.

These problems are addressed by the various aspects of the invention set out below which may be used separately or in any combination.

BRIEF SUMMARY OF THE INVENTION

In a first aspect, the invention provides apparatus for producing a pulse of light, comprising a light source operable to produce a said pulse of light, and a filter for filtering undesired light output frequencies from said pulse, characterised in that said filter comprises water.

The water acts as an ideal infra-red filter for apparatus to be used in treating the skin, because it is mainly the water content of the skin which adsorbs infra-red energy to produce undesirable generalised heating in photo-treatments.

Preferably, the apparatus comprises means for defining a flow path for said water, which means is optically transparent at least in a region in which said water acts as said filter, and means for producing a flow of said water through said flow path.

The light source preferably forms part of the means defining said flow path for water, whereby said water acts both to filter said light pulse and to cool said light source.

The distance traveled through the water by the light rays on average is preferably at least 1 cm, more preferably at least 1.5 cm. It may be selected to achieve 50% attenuation of the output at 1200 nm of the lamp.

This aspect of the invention includes the use of water as an infra-red absorbing filter in apparatus for the cosmetic or therapeutic photo-treatment of the human or animal body.

Photo-treatment apparatus has been described previously, e.g. in EP-A-0565331, which features a light guide to be placed against the skin. Non-contacting light guides terminating in focussing lenses are also known for use in photo-treatment apparatus, e.g. in U.S. Pat. No. 3,327,712. The light guide in EP-A-0565331 has a flat distal end for making contact with the skin. We have now discovered that it is advantageous to provide a convex curved distal end in such a light guide. Pressing the curved surface of the light guide against the skin in depilation treatment one or two millimeters into the tissue leads to removal of haemoglobin and oxyhaemoglobin from the light path towards a hair follicle. Haemoglobin and oxyhaemoglobin absorb the energy in the bandwidths used for depilation. By gently pressing the haemoglobin and oxyhaemoglobin away with the curved tip of the light guide, more energy is delivered to the target chromophore (melanin at the hair bulb) with a lower energy output than previously (i.e. there is an improved ratio between useful and damaging heat absorptions). Furthermore, the curved shape allows the light guide to slide easily over the skin when covering treatment areas larger than the "foot print" of the light guide.

In a variant of the first aspect of the invention there is provided an apparatus for producing a pulse of light, comprising a light source operable to produce a said pulse of light, and a filter for filtering undesired light output frequencies from said pulse, characterised in that said filter comprises a liquid within a conduit and the apparatus further comprises means defining a flow path for said liquid, a port of said flow path being constituted by said conduit and means for passing said liquid through said flow path.

Accordingly, in a second aspect, the invention provides photo-treatment apparatus comprising a light source and means for transmitting light output from the light source to a treatment site, said means including a light guide having a distal end for contacting the skin of a patient for said photo-treatment, said light guide distal end being shaped in a convex curve whereby pressing the light guide gently against the skin of the patient reduces the amount of blood in the skin below the light guide.

Preferably, said light guide is shaped as a parallelepipedic prism with a bull-nosed projection on said distal end. The projection is preferably of uniform transverse cross-section.

Pressure should not be used by the operator when treating vascular lesions because the haemoglobin and oxyhaemoglobin are then the target.

Indeed, for use in such treatment, the invention provides, in a variant of its second aspect, photo-treatment apparatus comprising a light source and means for transmitting light output from the light source to a treatment site, said means including a light guide having a distal end for contacting the skin of a patient for said photo-treatment, said light guide distal end being shaped in a concave manner whereby to relieve pressure applied to the skin by the light guide in regions where blood is a target of said light output.

According to the prior art, the power supply typically comprises a capacitor which is discharged to feed current through a series inductance and into the arc lamp. The prior art circuit creates a current pulse shaped approximately as one half period of a hyperbolic sine wave, rising from zero to a maximum and declining again to zero. We have found that the relatively gradual rise rate in the light power output at the commencement of each pulse is disadvantageous, as further described below.

In a third aspect, the present invention provides apparatus for producing a pulse of light, comprising:

a light source operable to provide an output of light in response to a power input, and a power supply connected to the light source for providing said power input, wherein said power supply is operable to provide a power output pulse or pulse train to drive said light source, to produce a light output pulse or pulse train during which light output pulse or pulse train for at least 80% of the light output period the light power output is from 75 to 125% of the time-weighted average light power output during the light output period.

This implies a much more rapid rate of rise in power at the start of the pulse and a higher rate of fall in power at the end of the pulse than is provided by a hyperbolic sine wave pulse power profile. This aspect of the invention aims at driving the light source on a current pulse which typically is shaped approximately as a square wave. Although the power requirement is indicated above in terms of the light power output, it will be understood that this is generally dependent on there being an electrical power input into the lamp (i.e. the output of the power supply) satisfying similar requirements in terms of electrical power.

Preferably, for at least 90% of the light pulse light output period the power output is from 75% to 125%, more preferably 90 to 110%, of the time-weighted average power output during the pulse light output period, most preferably from 95 to 105% of said value. Alternatively, it is preferred that for at least 95% of the light output period the light power output is from 75 to 125% of the time-weighted average light power output during the light output period, more preferably from 90 to 110% of said average value and most preferably from 95 to 105% of said value.

The time weighted average power output is given by the formula:

$$\sum_t p_n \cdot t_n$$

where $p_n$ is the power p at time $t_n$ and t is the total pulse light output period $\Sigma t_n$.

Alternatively, the time from the commencement of the light pulse to the light pulse reaching full power is no more than 10 percent, more preferably no more than 1 percent of the light output period of the pulse.

Preferably, means is provided for adjusting said time-weighted average light power output.

Arc lamps may be driven at different current levels, outputting different levels of optical radiation. However, this causes an associated shift in the spectrum. Thus the variation of the radiation in the short wave length range, e.g. below 700 nm tends to vary more than the variation in the longer wave length range. For instance on recording the optical output spectral density generated while driving an arc lamp at 100% and at 50% of maximum rated current, it was found that the optical output spectral density at 900 nm dropped to 67% of the preceding value, whereas the output at about 480 nm dropped to about 40% of the respective preceding value.

The unfiltered optical radiation from a flash light source is mainly from 380 nm to 1250 nm. For depilation, optical radiation at wave lengths longer than 700 nm is favored for its ability to penetrate deeper into the skin. Thus, for this application the short wave length radiation is regarded as an unwanted output to be filtered away in optical filters. The result is an excessive power dissipation in the filters.

The changing spectrum of the arc lamp if driven on a varying current as provided by power supply units according to the prior art, also makes it very difficult to estimate the effective output after the filters. According to this aspect of the invention the lamp is driven on a substantially constant level of current, where the spectrum then is approximately unchanged and the energy delivered to the target is proportionate to the duration of the square wave pulse or pulses.

The generation of this kind of drive signal requires a different electric circuit, which operates with a higher intrinsic power loss compared to the circuits of the prior art. The invention therefore achieves the result referred to only at the cost of an increased power loss in the electric driving circuit. The shifting of the power loss to take place in the power supply unit rather in the optical filters is considered a major advantage, since power dissipated in the power supply unit may easily be kept away from the patient and from the sensitive optical components in the applicator.

The capability of the apparatus according to the invention of reducing the amplitude of the power output may be used to a substantial advantage. We have found that the skin epidermis is capable of dissipating a greater amount of energy input than the tissue in the hair follicle. The difference, which may be in the order of factor of 20, is attributed to the greater thermal conductivity in the epidermal region. This difference more than offsets the disadvantage of the lowered intensity at the hair follicles.

Hence, for a given irradiation input, the hair follicle is heated to a higher temperature than the epidermis. This means that it is possible to establish a level where the hair follicles may be killed without harming the epidermis. The exact level may vary depending on skin pigmentation and has to be established for the particular patient. The procedure of establishing a proper level is considered to lie within the capabilities of those skilled in the art. The apparatus according to the invention is capable of outputting a treatment signal at a power level which is accurately controlled, in order to provide just the desired irradiation input.

Preferably, a single light pulse is applied to each treatment location.

The duration of each such pulse may be up to 100 msec, e.g. from 2 to 100 msec, more preferably from 10 to 70 msec. Preferably, the pulses are relatively long and relatively low in power rather than delivering the same amount of energy to the treatment site by being higher in power and shorter. The latter is what is obtained using laser systems. In the case of depilation and vascular treatments, this allows advantage to be taken of the differing thermal relaxation times of the skin and the hair follicle, so that heat is permitted to be lost from the skin, preventing burning, while heat accumulates in the hair follicle or blood vessel. Thus, the optimum pulse duration can be determined according to a relaxation time based algorithm.

By way of further guidance, it is generally accepted that the relaxation time of a hair follicle varies according to the thickness of the individual hair such that it is about 15 ms for a thin hair, about 50 ms for thick hair such as pubic hair, and for normal thickness hair about 30 ms. It is preferable that the pulse duration is approximately equal to the relaxation time of the target hair follicle or other target structure. The relaxation time of the skin surface is only about 2 ms. Accordingly, even relatively short pulses (e.g. 5 ms) will heat the skin surface to about the temperature it would reach if the application of energy was continuous. However, because of the longer relaxation time of the hair follicles, these will not be heated to close to their equilibrium value by such short pulses. Accordingly, where a very short pulse time is used, it will be necessary to use a much higher light intensity per unit area in order to heat the hair follicles adequately, with as a consequence greater heating of the skin surface. When a relaxation time algorithm dictated pulse duration is used, the hair follicle is heated to a temperature closer to the maximum temperature it would reach under continuous illumination at the light intensity used, which may therefore be much reduced compared to that needed with a short pulse duration. The skin surface is better able to lose heat and accordingly remains acceptably cool whilst the hair follicle or other target structure is heated to a higher temperature, sufficient to cause the desired amount of damage to the target cells.

According to any of the various aspects of the invention the light source preferably comprises a gas-filled arc lamp. Preferably, said gas-filled arc lamp is a xenon or krypton lamp.

However, the use of long pulses (e.g. 15 msec. or more) may shorten the life of gas discharge lamps and accordingly, we prefer to divide each long pulse into a pulse train of closely spaced shorter pulses, each having the power profile specified above. The duration of each such shorter pulse may be from 2 to 25 msec and the spacing between such shorter pulses is preferably from up to 3 msec, e.g. 0.2 to 1.5 msec.

The total light output period of a pulse train is equal to the sum of the durations of the small pulses within the pulse train. This will differ from the duration of the pulse train because it omits the intervals between the pulses in the pulse train. Thus for a pulse train of $\chi$ pulses, each of duration $t_\chi$ and each spaced from the succeeding pulse by an interval $i_\chi$ the period of light output D of the pulse train is given by:

$$D = \Sigma t_\chi$$

and is related to the duration T of the pulse train by:

$$D = T - \Sigma i_\chi$$

For a single long pulse, the light output period of course equals the duration as there are no intervals and $\Sigma i_\chi = 0$.

The total light output period of the pulse train is related to the duration of the pulse train also by the duty cycle which is the fraction of the pulse train duration during which there is light output.

Because the use of longer pulse or pulse train durations allows a reduced maximum light intensity to be employed, in another aspect, the present invention provides an apparatus for producing a pulse of light, comprising a light source operable to provide an output of light in response to a power input, and a power supply connected to the light source for providing said power input, wherein said power supply is operable to provide a power output pulse or pulse train to drive said light source to produce said light output pulse or pulse train, such that the ratio of the maximum light intensity to the total light energy output is no more than 75 kw:1 kw sec$^{-1}$, preferably 50 kw:1 kw sec$^{-1}$.

The apparatus preferably further comprises a housing for said light source, an aperture defined by said housing and a reflector in said housing positioned to reflect a beam of light through said aperture.

The apparatus preferably further comprises an optical filter in the path of said light beam, said optical filter being adapted to pass only selected wavelengths of said light, preferably this is water.

If apparatus for photo-treatment is to be used for treating a variety of conditions, it will normally be necessary that the light output be filtered differently according to the condition treated. There will normally therefore be provided a plurality of filters having differing filter characteristics and it will often be a matter involving the safe operation of the apparatus that the filter or the appropriate one be in place before treatment commences.

Accordingly there is provided according to a further aspect of the invention apparatus for photo-treatment comprising a light source, means for receiving a filter adapted to pass only selected wavelengths of light so as to dispose said filter in a light path from said light source, sensor means for detecting the presence and/or nature of a said filter in said filter receiving means, and interlock means for preventing operation of said light source to carry out photo-treatment except when a said filter or a said filter appropriate to an intended photo-treatment is present in said receiving means and/or for providing an alarm signal if a said filter or appropriate filter is not present in said receiving means.

This may be achieved by placing an electrically resistive circuit path, e.g. a resistive track, on the filter and providing means in the filter receiving means for measuring the electrical resistance of the track. Different filters will be provided with different resistances.

Alternatively, this may be achieved by a mechanical sensor detecting the presence of a filter in the filter receiving means, e.g. a sprung plunger which is depressed by the introduction of a filter and which actuates an electrical switch to make or break a circuit to allow operation of the apparatus. Different filters may be mechanically sensed by respective switches if they differ physically in thickness or shape. Preferably however there is at least one light source and at least one light sensor operatively arranged to observe the filtering activity of the filter on transmitted or reflected light and suitable electronic control means to determine the presence and optionally the nature of the filter from the light detected by said sensor or sensors.

The filters employed in photo-treatment apparatus of this type in the past have been of the interference type which comprise a non-filtering substrate bearing an extremely thin coating, typically of several layers of the order of the wavelength of light in thickness. We have found that at the high light intensities needed in photo-treatment apparatus, such filters are prone to damage. Any particle of dust on the filter surface can adsorb the light energy and become heated to a temperature which causes a pin-hole to form in the filter coating, allowing unfiltered light through.

The defect will progressively increase in size with further use and will eventually destroy the efficacy of the filter, producing progressively more severe burning of the skin.

Accordingly, there is provided according to a further aspect of the invention apparatus for photo-treatment comprising a light source, a filter adapted to pass only selected wavelengths of light disposed in a light path from said light source, said light source being adapted to produce a light flux of at least 250 J/cm$^2$/sec, wherein said filter is a non-interference absorption filter.

Such a filter is preferably of heat resistant glass or other heat resistant transparent material having a pigment distributed throughout its thickness. Additionally, a coated reflection filter may be formed on the surface of such a filter nearer the light source to reflect energy away so as to reduce adsorption in the filter and heating of the filter.

It is known to cool the lamp in this type of apparatus by circulating a cooling liquid, normally water, through channels in the material of the lamp housing. We have appreciated that this is a less than ideal approach. Accordingly, we prefer to provide means for circulating a cooling liquid in contact with said light source.

The cooling liquid may also circulate in contact with one or more filters for the light output. Thus, preferably, such apparatus further comprises a filter adapted to pass only selected wavelengths of light disposed in a light path from said light source and also in contact with said cooling liquid.

The cooling liquid is preferably water. Not only does water have a direct cooling function in the apparatus itself, we have appreciated that it acts as an ideal infra red filter, being adapted to filter out just those wavelengths which would cause unwanted heating of the skin of the patient, in which water is a principal infra red absorber. More generally as indicated in relation to the first aspect of the invention, the invention includes the use of water in the light path of photo-treatment apparatus as an infra red filter. Whilst this is preferably achieved by circulating the water over the lamp as a coolant as described above, water instead may be contained in a vessel in the light path to act purely as a filter. By the term 'water' in this context we include not only pure water but aqueous liquids generally, and in the case of the filter described above we include non-flowable transparent aqueous materials such as gels also.

As the coolant liquid may expand due to heating, the apparatus preferably includes a pressure relief device.

The power supply for driving the light source preferably comprises a capacitor, a charging circuit adapted for charging the capacitor to a preselected voltage, a resistor in series between said capacitor and said light source and a discharge switch operable to change from a non-conductive state to a conductive state to cause said capacitor to discharge said light source and back to said non-conductive state again.

Preferably, when the light source is an arc lamp the power supply comprises a simmer generator adapted for feeding the arc lamp with power at a level which is sufficient to keep the arc in the conductive state.

Optionally, the apparatus may include a light measuring device for measuring light reflected from or transmitted through the skin. The source of the light may be the main light source of the apparatus or may include a respective light source providing light to be reflected by the tissue. The measurement of the reflection of particular wavelengths or wavelength bands of light may be used to form a judgement regarding the skin coloration which in turn may be used in calculating the appropriate photo-treatment.

The invention further provides a method of treating live tissue for cosmetic purposes using apparatus according to any aspect of the invention. Cosmetic treatments envisaged include hair depilation, tattoo removal, wrinkle smoothing, skin rejuvenation, removal of disfiguring skin ailments and birthmarks.

The invention further provides a method for treating live tissue for therapeutic purposes using apparatus according to any aspect of the invention. Therapeutic purposes envisaged comprise treatment for psoriasis, vascular traumas, telangiectasis, capillary hemangioma, cancerous cells, removal of birthmarks, etc. Such treatment methods include not only those in which the light acts directly on the tissues but also methods of photo-dynamic therapy in which the light acts on a substance applied to or administered to the body and activates the substance, e.g. cleaves a prodrug to release the active material at a treatment site or causes the production of singlet excited oxygen at said treatment site as described in "Chemistry in Britain" May 1998 pp 45-50.

BRIEF DESCRIPTION OF THE SEVERAL VIEWS OF THE DRAWINGS

Further objects, features and advantages of the invention will appear from the appended detailed description given with reference to the enclosed drawings, wherein

FIG. 2 illustrates a transverse cross-section through a photo-treatment apparatus according to the invention including for use with the power supply arrangement of FIG. 1;

FIG. 3 is a longitudinal cross-section through the apparatus of FIG. 2;

FIG. 4 is a time chart of the current fed through the lamp of FIG. 1 during a pulse;

FIG. 6 shows three pulse trains suitable for depilation treatment.

FIG. 10 shows a light guide for use in accordance with the second aspect of the invention and as an aid for focussing the light output to a distance below the skin in apparatus as shown in FIGS. 1 to 3; and FIG. 11 shows a second form of light guide suitable for use when treating blood vessel disorders.

All drawings are schematic, illustrating only the principal features of the apparatus, including those essential to enable those skilled in the art to practise the invention whereas other features are omitted from the drawings for the sake of clarity. Throughout the drawings the same references are used to designate identical or similar features.

DETAILED DESCRIPTION OF THE INVENTION

Figure 1:
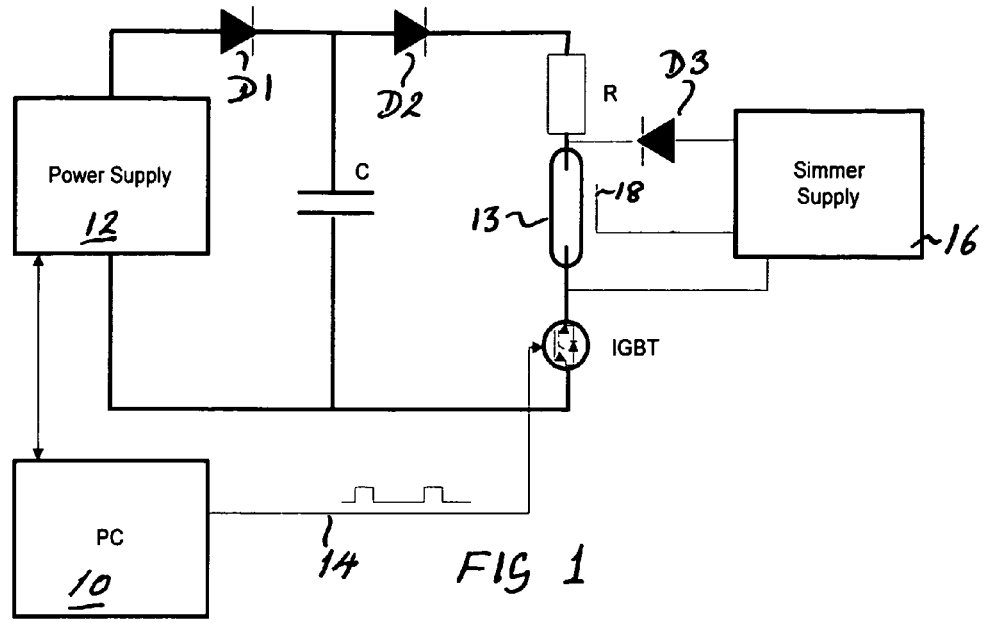
FIG. 1 illustrates a circuit diagram of a power supply with a lamp according to the invention.

Reference is first made to FIG. 1 illustrating the driving circuit and the lamp.

The circuit in FIG. 1 comprises a control unit in the form of a personal computer 10 (PC) used to control the system. The PC is connected to a power supply 12 which is adapted to charge through the diode D1 the capacitor C. In a preferred embodiment the power supply is adapted to charge the capacitor to a voltage set from the PC to a level in the range from 100-1000 volts. In a preferred embodiment the capacitance of the capacitor C is 10 to 100 mF.

The capacitor C is connected through diode D2 and resistor R to the flash lamp 13. The circuit is completed by a solid state switch IGBT, which is in the preferred embodiment implemented in the form of an isolated gated bi-polar transistor. The IGBT is controlled from the PC by a line 14. The IGBT is capable of changing from non-conductive to conductive state, of carrying currents in the range of 500 A and of changing from conductive to non-conductive state again, breaking this current.

On the right hand side of FIG. 1 a simmer power supply 16 is illustrated. This power supply is capable of feeding the flash lamp through the diode D3 with a simmer current in the order of 100 mA. In order to ignite the flash lamp the simmer power supply outputs a short pulse at a voltage of about 10-20 kilovolts on an electrode 18. The simmer current maintains a narrow arc inside the gas-filled lamp to keep this lamp in the conductive state.

Reference is now made to FIG. 2 illustrating a vertical transverse section through an applicator according to the invention. The applicator comprises housing 20, lamp 13, and a reflector 22 surrounding the lamp, long wave pass filter 25, light guide 27 and pressure relief o-rings 28. The reflector 22 is of ceramic and lines a U-shaped channel in a block of stainless steel 30. A second block of stainless steel 32 is bolted over the reflector. The filter 25 is sandwiched between blocks 30, 32 and is spaced from each of them by o-ring seals 28. The light output guide 27 is received in an opening in the block 32 and is supported by a rectangular section collar 34. The reflector 22 is shaped to direct the light output of the lamp upwards as illustrated in the figure. The edge of the reflector 22 constitutes a light output aperture.

The reflector together with the filter 25 forms a chamber 24 which is filled with water. As shown in FIG. 3, the block 30 has a tubular cavity in which the lamp 13 is received and is sealingly supported by o-rings 36. A water inlet 38 and a water outlet 40 communicate with respective annular spaces surrounding the ends of the lamp 13, which communicate also with and form part of the chamber 24.

An alternative form of pressure relief device (not shown) comprises a bulb-like expanded chamber filled with air and in fluid communication with the chamber 24. This air-filled chamber acts like a spring capable of smoothing out any pressure shocks in the water chamber that may be caused by the sudden discharges of the lamp.

The long wave pass filter 25 is adapted to absorb a part of the light in the near UV range e.g. UV and near UV shorter than 510 nm. It is a heat resistant glass filter of the non-interference type. IR light is absorbed by the water.

Optionally an additional removable filter may be provided between the proximal end of the light guide 27 and the filter 25. This may be removable and changeable by the user.

One may thus pass light of wavelength from 510 to 600 nm, e.g. 510 to 590 nm, according to the therapeutic requirement.

The removable filter is then chosen according to the intended treatment and is of coloured heat resistant glass (optionally combined with coated reflection filters and coloured filters) and may be substituted with other filters of similar type in order that the operator may chose from a selection of filters with different optical band widths. It may be a band pass filter.

Reference is now made to FIG. 4 illustrating a time chart of the current fed through the Xenon lamp during a pulse of treatments. FIG. 4 illustrates a pulse of a duration of 100 ms. The pulse rises practically immediately to a level of 338 A and decays exponentially to about 276 A after 100 ms.

Thus, the circuit of the preferred embodiment approximates the desired square wave by a sloping exponential decay with a time constant depending on the capacitance of the capacitor, the series resistor R, and the current driven through the Xenon lamp. Generally, satisfactory results are achieved if the current decays from 100% to somewhere above 50% of the initial value.

Figure 5:
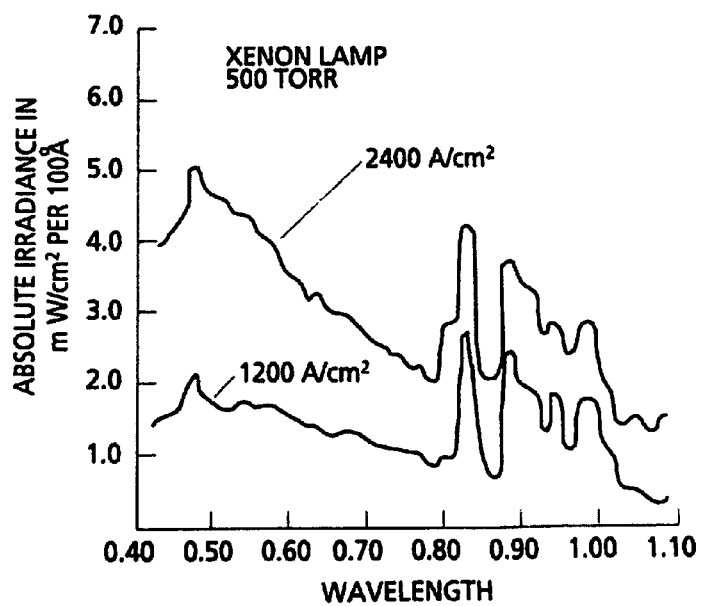
FIG. 5 is a chart of the luminous spectral density of the output of a Xenon lamp driven according to the prior art and the circuit of FIG. 1.

Reference is now made to FIG. 5 illustrating a chart of power spectral density of the radiation output by the Xenon lamp. FIG. 5 comprises two graphs, one drawn for a Xenon lamp at a current density of 2400 A per $cm^2$ and illustrating the optical output from a wave length about 420 nm up to about 1100 nm, the other curve showing the output of a current at half of this level. The curve illustrates the fact that the spectral output drops in a frequency dependent manner on the reduction of the drive current. For instance at 900 nm the output drops to approximately 65% while the output at 480 nm drops to about 40%, both taken relative to the respective preceding values.

FIG. 6 shows three different pulse trains for electrical power input suitable for use as depilation treatment using the apparatus of the invention. Pulse train (a) consists of five pulses of 3 ms duration spaced by delay intervals of 1.5 ms. The light output period of the pulse train is therefore 15 ms. The time weighted current average of the pulse train is 280 A and the maximum and minimum values are 300 A and 250 A respectively. Thus for essentially 100% of the light output period, the power will be within the 75% to 125% of average band. This is an example of a pulse train suitable for use in depilation of thin hairs.

The pulse train in (b) comprises four pulses of 5 ms with an interval of 1.5 ms. The average, maximum and minimum currents are 250, 285 and 200 A and again this is within the 75% to 125% of average band for essentially 100% of the light output period. This is suitable for depilation of normal hairs.

In (c) the average, maximum and minimum currents are 150, 190 and 95 A and the power is within the 75% to 125% band for approximately 80% of the light output period. The illustrated pulse train is suitable for depilation of thick hairs.

For each individual short pulse in each pulse train illustrated, the requirement for a power within the 75% to 125% of average power is met for at least 90% of the light output period.

Figure 7:
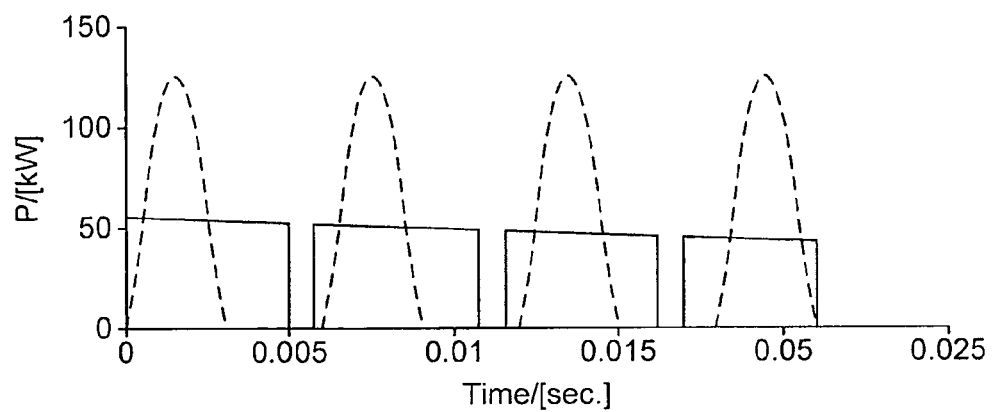
FIG. 7 shows a plot of light output power against time produced by machine settings for thin hair.
Figure 8:
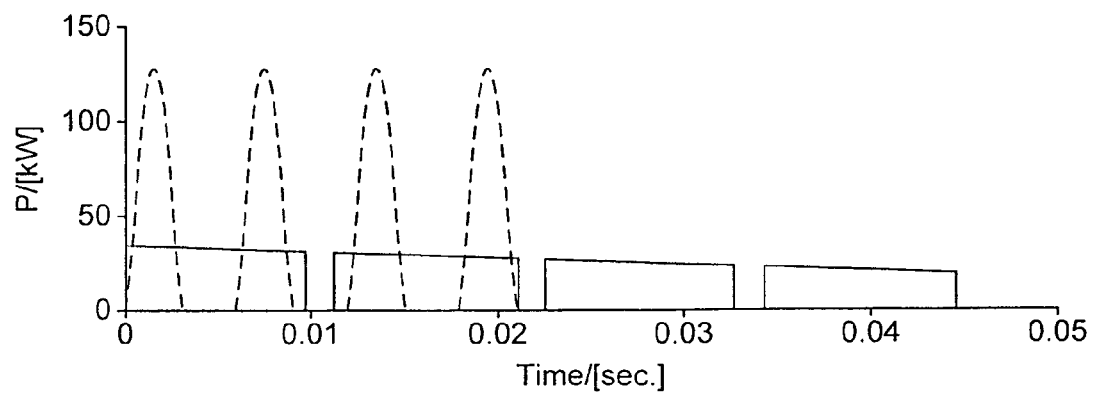
FIG. 8 shows a similar graph for machine settings for thick hairs.
Figure 9:
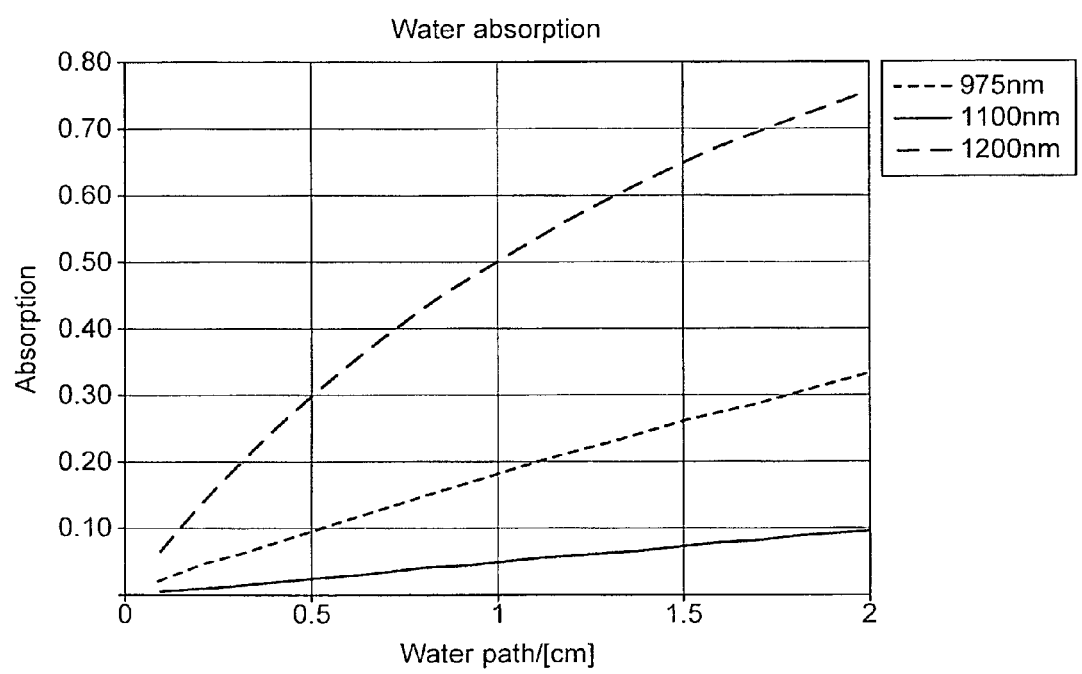
FIG. 9 shows a plot of light absorbance by different distances traveled in water.

FIG. 7 shows a plot of light output power in kW against time in seconds for a typical apparatus according to the invention (solid lines) compared to a commercially available machine (dotted lines), both being adjusted for thin hair. It will be seen that by comparison, the light output period of the apparatus of the invention is longer and the maximum power lower, although the energy output (area under each graph) is the same. FIG. 8 shows the same but with the adjustment set for thick hairs. The effect is even more pronounced. The ratio of peak output power to energy supplied in FIG. 7 is about 50 $sec^{-1}$ for the apparatus according to the invention, but 130 $sec^{-1}$ for the conventional machine, whereas in FIG. 8 the ratios are about 30 $sec^{-1}$ and about 130 $sec^{-1}$, respectively.

In order to use the system for treatment, an operator would place the applicator adjacent a selected treatment area and set the control unit to carry out an initialization routine. As part of this routine, the operator would enter data into the control unit concerning the patient and the type of treatment desired. Optionally, the control unit is programmed to ignite the flash lamp and burn it on the simmer power supply in order provide a low level of irradiation, by which the control unit through the utilization of a photo-detector will establish the reflectivity or transmission value of the treatment area. These data enable the control unit to suggest an appropriate irradiation scheme, which may comprise pulse level and pulse duration.

Once the operator has accepted the treatment scheme, he will only need to move the applicator to the respective treatment areas and activate a flash trigger, while the control unit will verify that contact is established, and that the reflectivity has the presumed value, and will then output the appropriate treatment signal.

As shown in FIG. 10, the apparatus may include a light guide with a curved distal end. The illustrated light guide is a parallelipedic prism 60 of rectangular transverse cross-section which has at its distal end a bull-nosed projection 62, such that in side view (on its smaller side face) the light guide is as shown in FIG. 10 and is of constant cross-section. The convex nose of the light guide can be pressed against the skin 64 to reduce (oxy)haemoglobin absorption of the light as described above by driving blood out of capillaries 66 and compressing larger vessels 68 to reduce blood flow. The convex curve may also serve as means for focussing the light output to concentrate it at a selected level below the skin. This reduces the energy density at the skin surface for a given energy density at the treatment site. The focussing depth may be made adjustable by a focussing mechanism or by the provision of separate lenses that may be swapped or supplemented with one another.

As shown in FIG. 11, instead of the light guide 11 having a convex nose to compress surface blood vessels, the light guide may on the contrary have a concave nose in order to minimise the pressure applied to surface blood vessels by contact with the light guide. This will be desirable when the blood vessels are themselves the target of the treatment.

Although various components, systems and methods have been explained in particular settings above, this is not to exclude that such components, systems or methods might be applied in other settings or applied differently. The particular examples mentioned have only been mentioned with the purpose of facilitating the understanding of the invention and not with the purpose of limiting the scope whereof which is defined exclusively by the appended patent claims.

The invention claimed is:

1. Apparatus for pulsed light cosmetic or therapeutic photo-treatment of the human or animal body, comprising a housing, a gas filled arc lamp light source within said housing operable to produce a pulsed light output, a power supply connected to said arc lamp light source for operation thereof to produce a light output duration of from 10 to 70 msec, a light output aperture defined by said housing, and a filter system for filtering undesired light output wavelengths from said pulse to produce a filtered light pulse for application to said body, at least part of said filter system being interposed between said light source and said aperture, wherein said filter system consists of (a) a filter for filtering out UV and near UV wavelengths shorter than 510 nm and for passing longer wavelengths and (b) water, said water being located in the apparatus for filtering out undesired skin heating wavelengths of light which would otherwise pass to said output aperture, wherein said filtered light pulse has an energy of at least 250 J/cm2/sec.

2. Apparatus as claimed in claim 1, comprising means for defining a flow path for said water, which means is optically transparent at least in a region in which said water acts as said filter, and means for producing a flow of said water through said flow path.

3. Apparatus as claimed in claim 2, wherein said light source forms part of the means defining said flow path for water, whereby said water acts both to filter said light pulse and to cool said light source.

4. Apparatus as claimed in claim 2, wherein a flow path defined by said means for defining a flow path forms a closed circuit around which said water circulates.

5. Apparatus as claimed in claim 1, further comprising a light guide for transmitting light output from said light source to a treatment site, said light guide having a proximal end receiving light from said aperture and having a distal end for contacting the skin of a patient for said photo-treatment, said light guide distal end being shaped in a convex curve whereby pressing the light guide gently against the skin of the patient reduces the amount of blood in the skin below the light guide.

6. Apparatus as claimed in claim 5, wherein said light guide is shaped as a parallelipedic prism with a bull-nosed projection on said distal end.

7. Apparatus as claimed in claim 1, further comprising a light guide for transmitting light output from said light source to a treatment site, said light guide having a proximal end receiving light from said aperture and having a distal end for contacting the skin of a patient for said photo-treatment, said light guide distal end being shaped in a concave manner whereby to relieve pressure applied to the skin by the light guide in regions where blood is a target of said light output.

8. Apparatus as claimed in claim 1, further comprising a power supply connected to the light source for providing power input to the light source, wherein said power supply is operable to provide a power output pulse or pulse train to drive said light source to produce said light output pulse or pulse train, during which light output pulse or pulse train for at least 80% of the light output period (i.e. the duration of a single pulse or the aggregate of the duration of the pulses within a pulse train excluding intervals between pulses) the light power output is from 75 to 125% of the time-weighted average light power output during the light output period.

9. Apparatus as claimed in claim 8, wherein for at least 90% of the light output period the light power output is from 75 to 125% of the time-weighted average light power output during the light output period.

10. Apparatus as claimed in claim 8, wherein means is provided for adjusting said time-weighted average light power output.

11. Apparatus as claimed in claim 1, further comprising a filter mounting for receiving a second filter having high filtration characteristics suitable to pass only selected wavelengths of light so as to dispose said second filter in a light path from said light source which light path also includes said filter comprising water, sensor means for detecting the presence and nature of a said second filter in said filter mounting, and interlock means for preventing operation of said light source to carry out photo-treatment except when a said second filter appropriate to an intended photo-treatment is present in said mounting and/or for providing an alarm signal if a said appropriate second filter is not present in said mounting.

12. Apparatus as claimed in claim 1, wherein said gas-filled arc lamp is a xenon or krypton lamp.

13. Apparatus as claimed in claim 8, wherein the power supply is coupled to a capacitor, a charging circuit adapted for charging the capacitor to a preselected voltage, a resistor in series between said capacitor and said light source and a discharge switch operable to change from a non-conductive state to a conductive state to cause said capacitor to discharge said light source and back to said non-conductive state again.

14. Apparatus according to claim 13, wherein the light source is an arc lamp and the power supply comprises a simmer generator adapted for feeding the arc lamp with power at a level which is sufficient to keep the arc in the conductive state.

* * * * *